(12) United States Patent
Gordon

(10) Patent No.: US 12,150,858 B2
(45) Date of Patent: *Nov. 26, 2024

(54) LOW-PROFILE INTERCRANIAL DEVICE

(71) Applicant: THE JOHNS HOPKINS UNIVERSITY, Baltimore, MD (US)

(72) Inventor: Chad Gordon, Cockeysville, MD (US)

(73) Assignee: The Johns Hopkins University, Baltimore, MD (US)

( * ) Notice: Subject to any disclaimer, the term of this patent is extended or adjusted under 35 U.S.C. 154(b) by 35 days.

This patent is subject to a terminal disclaimer.

(21) Appl. No.: 17/357,115

(22) Filed: Jun. 24, 2021

(65) Prior Publication Data
US 2021/0322172 A1 Oct. 21, 2021

Related U.S. Application Data

(63) Continuation of application No. 15/756,010, filed as application No. PCT/US2016/030447 on May 2, 2016, now Pat. No. 11,058,541.

(Continued)

(51) Int. Cl.
A61F 2/28 (2006.01)
A61B 5/00 (2006.01)
(Continued)

(52) U.S. Cl.
CPC .......... *A61F 2/2875* (2013.01); *A61B 5/0006* (2013.01); *A61B 5/0013* (2013.01); *A61B 5/0036* (2018.08); *A61B 5/0066* (2013.01); *A61B 5/031* (2013.01); *A61B 5/369* (2021.01); *A61B 5/4836* (2013.01); *A61B 5/686* (2013.01); *A61B 5/6868* (2013.01); *A61F 2/30942* (2013.01); *A61N 1/00* (2013.01);
(Continued)

(58) Field of Classification Search
CPC ......... A61F 2002/30948; A61B 5/6868; A61B 5/0066; A61B 5/031; A61B 5/0013
See application file for complete search history.

(56) References Cited

U.S. PATENT DOCUMENTS 3,457,922 A 7/1969 Ray
4,183,249 A 1/1980 Anderson
(Continued)

FOREIGN PATENT DOCUMENTS

CN 101528158 A 9/2009
CN 105286847 A 2/2016
(Continued)

OTHER PUBLICATIONS

Non-Final Office Action in corresponding U.S. Appl. No. 16/707,551 mailed on May 12, 2021, 6 pages.
(Continued)

*Primary Examiner* — Dinah Baria
(74) *Attorney, Agent, or Firm* — Harrity & Harrity, LLP

(57) ABSTRACT

Provided is a functional, low-profile intercranial device (LID). The LID includes a base portion; at least one cavity associated with the base portion and configured to accept at least one functional component; and at least one conduit having a first end in communication with the at least one cavity. The at least one functional component includes a medicinal, electronic, or optic therapeutic. The at least one conduit is configured to accept the medicinal therapeutic and a second end configured to dispense the therapeutic.

20 Claims, 6 Drawing Sheets

Related U.S. Application Data

(60) Provisional application No. 62/214,702, filed on Sep. 4, 2015.

(51) Int. Cl.
    *A61B 5/03*           (2006.01)
    *A61B 5/369*         (2021.01)
    *A61F 2/30*           (2006.01)
    *A61N 1/00*          (2006.01)
    *A61N 1/05*          (2006.01)
    *A61N 1/36*          (2006.01)
    *A61F 2/48*           (2006.01)
    *A61M 5/142*        (2006.01)

(52) U.S. Cl.
CPC ......... *A61N 1/0531* (2013.01); *A61N 1/3605* (2013.01); *A61B 5/0084* (2013.01); *A61B 5/4839* (2013.01); *A61F 2002/3067* (2013.01); *A61F 2002/3068* (2013.01); *A61F 2002/30948* (2013.01); *A61F 2/482* (2021.08); *A61M 5/14276* (2013.01); *A61M 2210/0687* (2013.01); *G06T 2207/20128* (2013.01)

(56) References Cited

U.S. PATENT DOCUMENTS

| | | |
|---|---|---|
| 4,206,762 A | 6/1980 | Cosman |
| 4,436,684 A | 3/1984 | White |
| 4,660,568 A | 4/1987 | Cosman |
| 4,805,634 A | 2/1989 | Ulrich et al. |
| 5,279,575 A | 1/1994 | Sugarbaker |
| 5,545,226 A | 8/1996 | Wingo et al. |
| 5,741,215 A | 4/1998 | DUrso |
| 5,752,962 A | 5/1998 | D'Urso |
| 5,810,712 A | 9/1998 | Dunn |
| 5,951,498 A | 9/1999 | Arnett |
| 6,006,124 A | 12/1999 | Fischell et al. |
| 6,016,449 A | 1/2000 | Fischell et al. |
| 6,061,593 A | 5/2000 | Fischell et al. |
| 6,079,681 A | 6/2000 | Stern et al. |
| 6,112,109 A | 8/2000 | DUrso |
| 6,120,290 A | 9/2000 | Fukushima et al. |
| 6,226,548 B1 | 5/2001 | Foley et al. |
| 6,248,126 B1 | 6/2001 | Lesser et al. |
| 6,254,639 B1 | 7/2001 | Peckitt |
| 6,285,902 B1 | 9/2001 | Kienzle, III et al. |
| 6,354,299 B1 | 3/2002 | Fischell et al. |
| 6,366,813 B1 | 4/2002 | DiLorenzo |
| 6,427,086 B1 | 7/2002 | Fischell et al. |
| 6,485,464 B1 | 11/2002 | Christenson et al. |
| 6,491,699 B1 | 12/2002 | Henderson et al. |
| 6,500,179 B1 | 12/2002 | Masini |
| 6,560,486 B1 | 5/2003 | Osorio et al. |
| 6,608,628 B1 | 8/2003 | Ross et al. |
| 6,618,623 B1 | 9/2003 | Pless et al. |
| 6,726,678 B1 | 4/2004 | Nelson et al. |
| 6,796,986 B2 | 9/2004 | Duffner |
| 6,819,956 B2 | 11/2004 | DiLorenzo |
| 6,845,175 B2 | 1/2005 | Kopelman et al. |
| 6,882,881 B1 | 4/2005 | Lesser et al. |
| 6,931,284 B2 | 8/2005 | Engmark et al. |
| 6,932,842 B1 | 8/2005 | Litschko et al. |
| 7,050,877 B2 | 5/2006 | Iseki et al. |
| 7,113,841 B2 | 9/2006 | Abe et al. |
| 7,158,833 B2 | 1/2007 | Pless et al. |
| 7,209,787 B2 | 4/2007 | DiLorenzo |
| 7,212,864 B2 | 5/2007 | Wahlstrand et al. |
| 7,231,254 B2 | 6/2007 | DiLorenzo |
| 7,242,982 B2 | 7/2007 | Singhal et al. |
| 7,242,984 B2 | 7/2007 | DiLorenzo |
| 7,263,401 B2 | 8/2007 | Scott et al. |
| 7,277,758 B2 | 10/2007 | DiLorenzo |
| 7,324,851 B1 | 1/2008 | DiLorenzo |
| 7,346,391 B1 | 3/2008 | Osorio et al. |
| 7,392,089 B2 | 6/2008 | Wahlstrand et al. |
| 7,510,557 B1 | 3/2009 | Bonutti |
| 7,529,856 B2 | 5/2009 | Wahlstrand et al. |
| 7,565,199 B2 | 7/2009 | Sheffield et al. |
| 7,596,399 B2 | 9/2009 | Singhal et al. |
| 7,596,408 B2 | 9/2009 | Singhal et al. |
| 7,647,097 B2 | 1/2010 | Flaherty et al. |
| 7,657,316 B2 | 2/2010 | Jaax et al. |
| 7,684,866 B2 | 3/2010 | Fowler et al. |
| 7,747,305 B2 | 6/2010 | Dean et al. |
| 7,747,318 B2 | 6/2010 | John et al. |
| 7,792,341 B2 | 9/2010 | Schutyser |
| 7,848,817 B2 | 12/2010 | Janzig et al. |
| 7,857,821 B2 | 12/2010 | Couture et al. |
| 7,894,905 B2 | 2/2011 | Pless et al. |
| 7,953,260 B2 | 5/2011 | Weinzweig et al. |
| 8,086,336 B2 | 12/2011 | Christensen |
| 8,096,997 B2 | 1/2012 | Plaskos et al. |
| 8,116,875 B2 | 2/2012 | Osypka et al. |
| 8,182,540 B2 | 5/2012 | Lin et al. |
| 8,221,430 B2 | 7/2012 | Park et al. |
| 8,221,461 B2 | 7/2012 | Kuiper et al. |
| 8,306,607 B1 | 11/2012 | Levi et al. |
| 8,357,165 B2 | 1/2013 | Grant et al. |
| 8,397,732 B2 | 3/2013 | Singhal et al. |
| 8,403,934 B2 | 3/2013 | Angibaud et al. |
| 8,428,315 B2 | 4/2013 | Suetens et al. |
| 8,454,701 B2 | 6/2013 | Devauchelle et al. |
| 8,457,744 B2 | 6/2013 | Janzig et al. |
| 8,518,085 B2 | 8/2013 | Winslow et al. |
| 8,535,063 B1 | 9/2013 | Amato |
| 8,591,562 B2 | 11/2013 | D'Ambrosio et al. |
| 8,650,005 B2 | 2/2014 | Liao |
| 8,706,285 B2 | 4/2014 | Narainasamy et al. |
| 8,761,889 B2 | 6/2014 | Wingeier et al. |
| 8,781,557 B2 | 7/2014 | Dean et al. |
| 8,827,932 B2 | 9/2014 | Hirabayashi |
| 8,840,556 B2 | 9/2014 | Lin et al. |
| 8,938,290 B2 | 1/2015 | Wingeier et al. |
| 8,965,513 B2 | 2/2015 | Wingeier et al. |
| 9,014,810 B2 | 4/2015 | Sauter-Starace et al. |
| 9,044,195 B2 | 6/2015 | Manwaring et al. |
| 9,084,901 B2 | 7/2015 | Wahlstrand |
| 9,162,072 B2 | 10/2015 | Singhal et al. |
| 9,179,850 B2 | 11/2015 | Wingeier et al. |
| 9,208,558 B2 | 12/2015 | Dean et al. |
| 9,216,084 B2 | 12/2015 | Gordon et al. |
| 9,330,206 B2 | 5/2016 | Dean et al. |
| 9,393,432 B2 | 7/2016 | Wahlstrand et al. |
| 9,421,363 B2 | 8/2016 | Krahl et al. |
| 9,421,371 B2 | 8/2016 | Pless et al. |
| 9,440,064 B2 | 9/2016 | Wingeier et al. |
| 9,462,958 B2 | 10/2016 | Osorio et al. |
| 9,474,611 B2 | 10/2016 | Restrepo et al. |
| 9,522,081 B2 | 12/2016 | D'Ambrosio et al. |
| 9,592,124 B2 | 3/2017 | Joganic |
| 9,592,377 B2 | 3/2017 | Greenberg et al. |
| 9,659,152 B2 | 5/2017 | Mueller |
| 9,993,337 B1 | 6/2018 | Brogan et al. |
| 10,537,337 B2 | 1/2020 | Gordon et al. |
| 11,058,541 B2 | 7/2021 | Gordon |
| 11,446,148 B2 | 9/2022 | Gordon et al. |
| 11,589,992 B2 | 2/2023 | Christopher et al. |
| 2001/0021851 A1 | 9/2001 | Eberlein et al. |
| 2002/0002390 A1 | 1/2002 | Fischell et al. |
| 2002/0035458 A1 | 3/2002 | Kim et al. |
| 2002/0165552 A1 | 11/2002 | Duffner |
| 2002/0169485 A1 | 11/2002 | Pless et al. |
| 2003/0125786 A1 | 7/2003 | Gliner et al. |
| 2004/0073270 A1 | 4/2004 | Firlik et al. |
| 2004/0091845 A1 | 5/2004 | Azerad et al. |
| 2004/0172044 A1 | 9/2004 | Grimm et al. |
| 2004/0176816 A1 | 9/2004 | Singhal et al. |
| 2004/0176818 A1 | 9/2004 | Wahlstrand et al. |
| 2004/0204760 A1 | 10/2004 | Fitz et al. |
| 2005/0003268 A1 | 1/2005 | Scott et al. |
| 2005/0004637 A1 | 1/2005 | Singhal et al. |
| 2005/0043835 A1 | 2/2005 | Christensen |
| 2005/0113846 A1 | 5/2005 | Carson |

(56) References Cited

U.S. PATENT DOCUMENTS

| | | |
|---|---|---|
| 2005/0117696 A1 | 6/2005 | Suzuki et al. |
| 2005/0203366 A1 | 9/2005 | Donoghue et al. |
| 2005/0245984 A1 | 11/2005 | Singhal et al. |
| 2006/0122578 A1 | 6/2006 | Lord et al. |
| 2006/0142657 A1 | 6/2006 | Quaid et al. |
| 2006/0195111 A1 | 8/2006 | Couture |
| 2006/0224242 A1 | 10/2006 | Swords et al. |
| 2007/0038100 A1 | 2/2007 | Nita |
| 2007/0167701 A1 | 7/2007 | Sherman |
| 2007/0179558 A1 | 8/2007 | Gliner et al. |
| 2007/0207441 A1 | 9/2007 | Lauren |
| 2007/0225773 A1 | 9/2007 | Shen et al. |
| 2008/0140149 A1 | 6/2008 | John et al. |
| 2008/0304725 A1 | 12/2008 | Leitner |
| 2008/0306490 A1 | 12/2008 | Akin et al. |
| 2008/0319448 A1 | 12/2008 | Lavallee et al. |
| 2009/0088674 A1 | 4/2009 | Caillouette et al. |
| 2009/0092948 A1 | 4/2009 | Gantes |
| 2009/0099570 A1 | 4/2009 | Paradis et al. |
| 2009/0112273 A1 | 4/2009 | Wingeier et al. |
| 2009/0112278 A1 | 4/2009 | Wingeier et al. |
| 2009/0220122 A1 | 9/2009 | Richards et al. |
| 2009/0240141 A1 | 9/2009 | Neubauer et al. |
| 2009/0281623 A1 | 11/2009 | Kast et al. |
| 2009/0311647 A1 | 12/2009 | Fang et al. |
| 2010/0145425 A1 | 6/2010 | Jung et al. |
| 2010/0145898 A1 | 6/2010 | Malfliet et al. |
| 2010/0261998 A1 | 10/2010 | Stiehl |
| 2010/0311028 A1 | 12/2010 | Albert et al. |
| 2011/0009814 A1 | 1/2011 | Tsoukalis |
| 2011/0029093 A1 | 2/2011 | Bojarski et al. |
| 2011/0066072 A1 | 3/2011 | Kawoos et al. |
| 2011/0071425 A1 | 3/2011 | Ludvig et al. |
| 2011/0087465 A1 | 4/2011 | Mahfouz |
| 2011/0102549 A1 | 5/2011 | Takahashi |
| 2011/0117530 A1 | 5/2011 | Albocher et al. |
| 2011/0196377 A1 | 8/2011 | Hodorek et al. |
| 2011/0208256 A1 | 8/2011 | Zuhars |
| 2011/0213382 A1 | 9/2011 | Decre et al. |
| 2011/0244415 A1 | 10/2011 | Batesole |
| 2011/0282191 A1 | 11/2011 | Brennan et al. |
| 2012/0010711 A1 | 1/2012 | Antonyshyn et al. |
| 2012/0041318 A1 | 2/2012 | Taylor |
| 2012/0041446 A1 | 2/2012 | Wong et al. |
| 2012/0063655 A1 | 3/2012 | Dean et al. |
| 2012/0109228 A1 | 5/2012 | Boyer et al. |
| 2012/0259592 A1 | 10/2012 | Liao |
| 2013/0035690 A1 | 2/2013 | Mittelstadt et al. |
| 2013/0122463 A1 | 5/2013 | Csillag |
| 2013/0204316 A1 | 8/2013 | Carpentier et al. |
| 2013/0204600 A1 | 8/2013 | Mehra |
| 2013/0211424 A1 | 8/2013 | Thiran et al. |
| 2013/0211792 A1 | 8/2013 | Kang et al. |
| 2013/0217996 A1 | 8/2013 | Finkelstein et al. |
| 2013/0247644 A1 | 9/2013 | Swoboda et al. |
| 2013/0296872 A1 | 11/2013 | Davison et al. |
| 2013/0297265 A1 | 11/2013 | Baloch et al. |
| 2013/0310963 A1 | 11/2013 | Davison |
| 2013/0345599 A1 | 12/2013 | Lin et al. |
| 2014/0045167 A1 | 2/2014 | Anderson et al. |
| 2014/0122382 A1 | 5/2014 | Elster et al. |
| 2014/0127639 A1 | 5/2014 | Hirabayashi |
| 2014/0249454 A1 | 9/2014 | Carpentier |
| 2014/0329194 A1 | 11/2014 | Sachdeva et al. |
| 2014/0330123 A1 | 11/2014 | Manwaring et al. |
| 2014/0343557 A1 | 11/2014 | Mueller |
| 2014/0350635 A1 | 11/2014 | Strother et al. |
| 2015/0038948 A1 | 2/2015 | Ludvig et al. |
| 2015/0157862 A1 | 6/2015 | Greenberg et al. |
| 2015/0217500 A1 | 8/2015 | Antonyshyn et al. |
| 2015/0272691 A1 | 10/2015 | Kim et al. |
| 2015/0289980 A1 | 10/2015 | Hirata et al. |
| 2015/0297103 A1 | 10/2015 | Hu et al. |
| 2015/0297309 A1 | 10/2015 | Bly et al. |
| 2015/0328004 A1 | 11/2015 | Mafhouz |
| 2016/0038243 A1 | 2/2016 | Miller et al. |
| 2016/0045317 A1 | 2/2016 | Lang et al. |
| 2016/0045723 A1 | 2/2016 | Bornzin et al. |
| 2016/0193048 A1 | 7/2016 | Prada |
| 2016/0263277 A1 | 9/2016 | Kim et al. |
| 2016/0296312 A1 | 10/2016 | Kuhn et al. |
| 2016/0324664 A1 | 11/2016 | Piron et al. |
| 2016/0346091 A1 | 12/2016 | Bin Abdul Rahman et al. |
| 2017/0014169 A1 | 1/2017 | Dean et al. |
| 2017/0049351 A1 | 2/2017 | Esteller |
| 2017/0049398 A1 | 2/2017 | Hirata et al. |
| 2017/0108930 A1 | 4/2017 | Banerjee et al. |
| 2017/0156596 A1 | 6/2017 | Aguilar-Mendoza et al. |
| 2017/0224968 A1 | 8/2017 | Utz et al. |
| 2017/0273797 A1 | 9/2017 | Gordon et al. |
| 2017/0368330 A1 | 12/2017 | Silay et al. |
| 2018/0286379 A1 | 10/2018 | Norris et al. |
| 2019/0030374 A1 | 1/2019 | Carpentier et al. |
| 2021/0315701 A1 | 10/2021 | Gordon |

FOREIGN PATENT DOCUMENTS

| | | |
|---|---|---|
| JP | 5746206 B2 | 7/2015 |
| WO | 2004093725 A2 | 11/2004 |
| WO | 2012147114 A1 | 11/2012 |
| WO | 2013101753 A1 | 7/2013 |
| WO | 2014043452 A1 | 3/2014 |
| WO | 2018064239 A1 | 4/2018 |
| WO | 2018076075 A1 | 5/2018 |
| WO | 2020180628 A1 | 9/2020 |
| WO | 2021050843 A1 | 3/2021 |
| WO | 2021050881 A1 | 3/2021 |

OTHER PUBLICATIONS

Examination Report in Australian Corresponding Application No. 2015353601 dated Jul. 29, 2019, 4 pages.

Examination Report in Australian Corresponding Application No. 2015353523 dated Jun. 28, 2019, 3 pages.

Extended European Search Report in Corresponding EP Application No. 16842453 dated Apr. 16, 2019, 8 pages.

Final Office Action in U.S. Appl. No. 15/100,229 dated Oct. 21, 2019, 48 pages.

Final Office Action in U.S. Appl. No. 15/100,241 dated Aug. 15, 2019, 27 pages.

Non Final Office Action n U.S. Appl. No. 15/100,252 dated Sep. 25, 2019, 9 pages.

Notice of Allowance in U.S. Appl. No. 15/100,258 dated Sep. 11, 2019, 6 pages.

Final Office Action in U.S. Appl. No. 15/529,042 dated Sep. 4, 2019, 9 pages.

Non Final Office Action in U.S. Appl. No. 15/100,256 dated Jun. 14, 2019, 13 pages.

Non-Final Office Action in corresponding U.S. Appl. No. 15/529,036 mailed on Apr. 27, 2021, 24 pages.

Ledesma et al., "Responsive Neurostimulation System (RNS) in setting of cranioplasty and history of multiple craniotomies", Interdisciplinary Neurosurgery: Advanced Techniques and Case Management, 2016, vol. 5, 3 pages.

International Search Report and Written Opinion mailed Sep. 12, 2016 for PCT/US2016/030447.

Aatman M. Shah, Henry Jung, and Stephen Skirboll, Materials used in cranioplasty: a history and analysis, Apr. 2014, pp. 1-7, Neurosurg Focus, vol. 26. DOI: 10.3171/2014.2.FOCUS13561.

A.E. Abdulai, M.I. Iddrissu and T.K. Dakurah, Cranioplasty Using Polymethyl Methacrylate Implant Constructed from an Alginate Impression and Wax Elimination Technique, Mar. 2006, pp. 18-21, vol. 40, No. 1, Ghana Medical Journal.

L.C. Hieu, E. Bohez, J. Vander Sloten, P. Oris, H.N. Phien, E. Vatcharaporn and P.H. Binh, Design and manufacturing of Cranioplasty Implants by 3-axis CNC Milling, Feb. 20, 2002, pp. 1-11, Technology and Health Care, IOS Press.

J. Tobias, K. Hynynen, R. Roemer, A.N. Guthkelch, A.S. Fleischer, J. Shively, An ultrasound window to perform scanned, focused

(56) References Cited

OTHER PUBLICATIONS ultrasound hyperthermia treatments of brain tumors, Mar./Apr. 1987, pp. 228-234, Medical Physics, vol. 14, No. 2.

Bell, R. B., "Computer Planning and Intraoperative Navigation in Orthognathic Surgery"; Journal of Oral and Maxillofacial Surgery; 2011, vol. 69, No. 3, pp. 592-605.

Cevidances, L. et al. Three-dimensional surgical simulation:, American Journal of Orhodontics and Dentofacial Orhopedics, vol. 138, Issue 3, Sep. 2010, pp. 361-371 (Year:2010).

Chapuis et al., "A new approach for 3D computer-assisted orthognathic surgery-first clinical case", Elsevier, International Congress Serier, vol. 1281, May 2005, pp. 1217-1222 (Year: 2005).

Chapuis, J. et al., "A New System for Computer-Aided Preoperative Planning and Intraoperative Navigation During Corrective Jaw Surgery", IEEE, Transactions on Information Technology in Biomedicine, vol. 11, No. 3, May 2007, pp. 274-287 (Year: 2007).

Extended European Search Report dated Jul. 27, 2018 in corresponding EP Application No. 15862375, 8 pages.

Extended European Search Report dated May 24, 2018 in corresponding EP Application No. 15862868, 8 pages.

Goh, R. et al., "Customized fabricated implats after previous failed cranioplasty", Journal of Plastic, Reconstructive and Aesthetic Surgery, vol. 63, 2010, pp. 1479-1484.

Gordon et al.; "Overcoming Cross-Gender Differences and Challenges in Le Fort-Based, Craniomaxillofacial Transplantation With Ehanced Computer-Assisted Technology"; Annals of Plastic Surgery; Oct. 2013, vol. 71, No. 4; pp. 421-428.

Internatinal Search Report and Written Opinion in International Application No. PCT/US2015/062521, 12 pages.

International Search Report and Written Opinion dated Mar. 9, 2015 from corresponding International Application No. PCT/US2014/067671; 13 pages.

International Search Report and Written Opinion in International Application No. PCT/US2015/062516, 10 pages.

International Search Report dated Feb. 24, 2015 from corresponding International Application No. PCT/US2014/067504; 5 pgs.

International Search Report dated Mar. 13, 2015 from corresponding International Application No. PCT/US2014/067167; 5 pgs.

International Search Report dated Mar. 20, 2015 from corresponding International Application No. PCT/US2014/067692; 4 pgs.

International Search Report dated Mar. 5, 2015 from corresponding International Application No. PCT/US2014/067174; 4 pgs.

International Search Report dated Mar. 5, 2015 from corresponding International Application No. PCT/US2014/067656; 5 pgs.

International Search Reported dated Feb. 24, 2015 from corresponding International Application No. PCT/US2014/067504; 11 pgs.

International Search Reported dated Feb. 27, 2015 from corresponding International Application No. PCT/US2014/067581; 4 pgs.

Jalbert et al., "One-step primary reconstruction for complex craniofocial re section with PEEK custom-made implants", Jounal of Cranio-Maxillo-Facial Surgery, Mar. 2014, vol. 42, No. 2, pp. 141-148.

Lee, M. et al., "Custom implant design for patients with craniel defects", Engineering in Medicine and Biology Magazine, IEEE, 2002, vol. 21, pp. 38-44.

Molla: "General Principles of Bone Grafting in Maxillofacial Surgery"; Jan. 2001; The ORION vol. 8; https://pdfs.semanticsholar.org/ec2e/7ba90a835e873687d9454a848842f26c4.pdf.

Murphy et al. "Computer-Assisted, Le Fort-Based, Face-Jaw-Teeth Transplantation: A Pilot Study on System Feasibility and Translational Assessment." International journal of computer assisted radiology and surgery, 2014.

Murphy et al., "Computer-assisted single-stage cranioplasty", IN: Engineering in Medicine and Biology Sociaty (EMBC), Aug. 25-29, 2015, pp. 4910-4912.

Schramm et al.; "Non-invasive Registration in Computer Assisted Craniomaxillofacial Surgery"; Rechner-und Sensorgestutzte Chirurgie, 2001, pp. 258-268.

LOW-PROFILE INTERCRANIAL DEVICE

CROSS-REFERENCE TO RELATED APPLICATIONS

This application is a continuation of U.S. application Ser. No. 15/756,010 filed Feb. 27, 2018, now allowed, which is a national phase application of PCT/US2016/030447 filed May 2, 2016, which claims priority to U.S. Provisional Patent Application Ser. No. 62/214,702 entitled "Functional Custom Craniofacial Implants" filed on Sep. 4, 2015, the entirety of all of which are incorporated by reference herein.

FIELD OF THE INVENTION

This invention relates generally to the field of surgery, particularly cranioplasty, craniomaxillofacial surgery and neurosurgery, and specifically to the field of customized craniofacial implants.

BACKGROUND OF THE INVENTION

Systemic delivery of medication to the brain is hindered by the blood-brain barrier's (BBB) highly selective permeability, which allows the highly-specified passage of only certain materials from capillary blood into the brain's extracellular fluid. In fact, recent reports state that over 60% of all pharmaceutical laboratories specific to neurologic medicine development are shutting down due to the complicated, gridlock barriers preventing successful delivery of blood-based medicines into the brain. As such, much work has been focused on engineering medicinal compositions to be small and hydrophobic enough to diffuse through the endothelial cells that make up the complex BBB. However, this has been suboptimal since many of the medicinally-advantageous compositions are simply too large or hydrophilic and are cannot be engineered for such direct delivery to the brain. As such, an improved anatomical location, such as improved position of patient-specific, pre-fabricated devices within the cranial bone space and strategy for enhanced delivery of battery-powered platforms capable of local neurological medicine delivery would be a welcome addition to the art.

Meanwhile, during cranioplasty procedures, diseased or damaged portions of the skull (craniectomy defects) are safely removed and replaced, while the brain is exposed underneath without injury. Following resection of diseased cranial bone, such craniectomy defects are often reconstructed with custom craniofacial implants (CCIs)—as opposed to using generic, "off-the-shelf" materials. Historically, however, cranioplasty patients requesting CCI-based reconstruction for an ideal appearance have been limited to "second-stage" operations in instances of pre-existing skull defects so that the exact fit and design could be obtained. However, recent modifications to the approach have allowed a few isolated surgical teams to perform "single-stage cranioplasties"—by which a clinician, such as a surgeon, manually reshapes/resizes a previously-ordered, custom implant (with oversized dimensions) to fit perfectly into the skull defect—as opposed to using "off-the shelf" materials. Either way, for single-stage methods involving skull tumors or second-stage cranioplasties for pre-defined skull defects, the advent of computer-aided design/manufacturing (CAD/CAM), has provided surgeons alike with perfectly-shaped CCIs designed and manufactured based in part on fine cut preoperative computed tomography (CT) scans and three-dimensional reconstruction (+/−stereolithographic models).

In fact, recent reports suggest that the use of CCIs can improve cosmesis, decrease operative times, prevent scalp-related wound complications, and enhance patient satisfaction—and therefore, they serve as an ideal medium for reconstructing neurosurgery patients. For example, International Patent Application No. PCT/US2014/067656, filed on Nov. 26, 2014 and entitled "Computer-Assisted Craniomaxillofacial Surgery," describes a recently-developed surgical workstation's with the novel ability to provide intraoperative visual guidance related to planned-versus-actual position of CCI (on intraoperative visual monitors)—following placement of the CCI within the three-dimensional craniofacial defect (in relation to virtual plan)—which ultimately adds even greater precision and simplicity to this complex operation. Similarly, all CCIs up until now have been used to replace abnormal bone having some form of disease, either of benign or malignant etiology. These customized skull implants may be termed "static CCIs" (SCCIs)—mainly because their main constant (i.e. unchanged purpose with respect to time) purpose encompasses strictly two benefits following placement—"brain protection" and "enhanced appearance".

Meanwhile, there are other "off the shelf" neurological implants that have functionality, such as delivering electrical impulses, but aren't customizable or designed to protect the brain. Most of these so called Functional Neurological implants (FNI) fall into two categories: Deep Brain Stimulators (DBS) and Cortical Brain Stimulators (CBS). Modern day neurologic devices are confronted and challenged with high extrusion and infection risk (i.e. current flaws in modern day devices leads to high incidence of extrusion through skin thereby requiring premature explantation) approaching 50%. Similarly, battery-powered, low-profile devices for intercranial placement currently do not exist on the market. As such, the field of neurosurgery has been hampered and limited in many areas including examples like battery-powered neuromodulation/cortical stimulation and delivery of neurological medicines.

But with increasing experience and now surgical complication rates exceedingly low, for the CCIs can also be modified in real-time for scenarios where more or less skull bone is removed and the skull defect dimensions do NOT match up perfectly to the pre-fabricated CCI (versus an originally envisioned, as designed in a planning stage)—including such associated methods of making the CCIs are described in U.S. Provisional Patent Application No. 62/155,311, filed on Apr. 30, 2015 and entitled "A Cutting Machine For Resizing Raw Implants During Surgery", U.S. Provisional Patent Application No. 62/117,782, filed on Feb. 18, 2015 and entitled "Computer-Assisted Cranioplasty"; and International Patent Application No. PCT/US14/67656, filed on Nov. 26, 2014 and entitled "Computer-Assisted Craniomaxillofacial Surgery", the disclosures of which are hereby incorporated by reference herein in their entireties.

Due to the recent reductions for time needed to design, fabricate and implant CCIs, more cranioplasty procedures with alloplastic implants are being performed around the world than ever before. Accordingly, these recent developments in CCI sterility, shape design, and streamline production—together provide an opportunity that extends CCI-based cranioplasty beyond only patients who require replacement of pre-existing craniectomy defects. Therefore, what is needed in the art, are new pre-fabricated, customized, patient-specific implantable devices with low-profiles (i.e. to avoid scalp-related complications and high extrusion risk leading to premature explantation). What is also needed in the art are corresponding methods of making and implanting such implant devices, including methods using computer-assisted surgical procedures, such as computer-assisted cranioplasty. Such improvements would exploit the benefits of direct access to the brain and ideal anatomical location/proximity provided by these novel CCIs placed directly on top and just a few millimeters away from the brain to deliver life-changing interventions provide an unprecedented method to deliver locally, for example, Neurologic Deep Brain stimulations, or neurologic medicines, that are otherwise prevented from diffusing through the blood-brain barrier via common delivery methods (i.e. oral, intravenous) and battery-powered functions via various encased components including neuromodulation devices, imaging devices, radiation therapy devices, and remote sensing/monitoring devices.

SUMMARY

In an embodiment, there is a functional, low-profile intercranial device (LID). The LID includes a base portion; at least one cavity associated with the base portion and configured to accept at least one functional component; and at least one conduit having a first end in communication with the at least one cavity. The functional component includes a medicinal therapeutic. The at least one conduit is configured to accept the medicinal therapeutic and a second end configured to dispense the therapeutic.

In another embodiment, the LID includes a base portion; and at least one cavity associated with the base portion and configured to accept at least one functional component. The functional includes a physiological condition intervention system.

In another embodiment, the LID includes a base portion; at least one cavity associated with the base portion and configured to accept at least one functional component; and a controller. The at least one cavity includes a first cavity and a second cavity, and the functional component includes a first functional component and a second functional component. The first functional component includes a medicinal therapeutic; at least one conduit that includes a first end in communication with the first cavity and configured to accept the medicinal therapeutic, and a second end configured to dispense the therapeutic. The controller is configured to initiate or terminate dispensing of the medicinal therapeutic. The second functional component comprises a physiological condition intervention system and at least one conduit configured to transmit a signal between the second functional component and a patient. The physiological condition intervention system includes: a power source; and a sensor powered by the power source and configured to sense a physiological condition. The controller is further configured to activate the power source, the sensor or both.

In another embodiment, there is a surgical method that includes replacing or removing an anatomical portion of a being and attaching a LID to the being. The LID comprises a base portion and at least one cavity associated with the base portion and configured to accept at least one functional component.

In another embodiment, there is a surgical method that includes removing an implant that is attached to a being; and attaching a low-profile intercranial device (LID) at a location on the being where the implant was located. The LID comprises a base portion and at least one cavity associated with the base portion and configured to accept at least one functional component.

An advantage of at least one embodiment provides a low-profile intercranial device (LID) that can replace either skull defects of any size following pathology-based resection and/or normal bone removal for brain-based intervention. In at least one embodiment, a LID includes one or more of a functional component for delivering radiation therapy and/or neurological medicines. In at least one embodiment, a LID includes one or more functional component for remote sensor-monitoring for abnormal levels of intracranial pressure (ICP) or brain activity (i.e. seizures), such as an electrical array for motor/vision cortex control, battery-based stimulation hardware for epilepsy management (grids/batteries/wires), low-profile remote imaging devices (e.g., optical coherence tomography (OCT), duplex ultrasound). Such functional components may or may not be directly connected to the brain via wiring/electrodes, an intra-ventricular catheter (IVC) for ventricle delivery, intra-neural wiring (for parenchymal delivery), and/or other conduit for blood vessels (for intravenous delivery). In at least one embodiment, a LID includes one or more of a functional component that has the ability to deliver and/or sense electrical impulses, take remote images/photographs of anatomical features, deliver neurologic medicines into the brain's blood vessels, ventricles of the brain, and/or directly into cerebral fluids. Accordingly, by at least one embodiment described herein, there is provided an intercranial device and/or method for circumventing the ever-challenging BBB, which in turn, can drastically increase efficacy for a variety of neurological diseases and at the same time reduce current toxic doses with high-frequency, adverse reaction profiles. Thus, at least some embodiments described herein provide for the removal of either diseased skull bone and/or normal skull bone—for patients in need of future neurological intervention (i.e. medicine delivery, remote monitoring, radiation therapy, neuromodultaion, etc.)—as a method to deliver medicines and/or electricity-based intervention in a safe way locally (using the valuable dead space within the standard CCI) and in turn eradicating the obstacles of the BBB and accompanying high extrusion rates of current day extracranial devices eroding through the scalp requiring premature removal. Such embodiments can be valuable for patients with brain-related disease, and thus require removal of normal healthy skull bone in exchange for enhanced treatment with minimal complication. Besides neurological medicines, other advantages of the embodiments provide a novel method and delivery system for local application of radiation therapy (via radioactive seeds housed within the implant), remote neuro-monitoing (i.e., optical coherence tomography), remote neuro-imaging (i.e. electroencephalogram (EEG)), and/or novel neuromodulation in streamlined fashion with encased, low-profile batteries and wiring all housed within the single, pre-fabricated implant.

Additional advantages of the embodiments will be set forth in part in the description which follows, and in part will be understood from the description, or may be learned by practice of the invention. The advantages will be realized and attained by means of the elements and combinations particularly pointed out in the appended claims.

It is to be understood that both the foregoing general description and the following detailed description are exemplary and explanatory only and are not restrictive of the invention, as claimed.

The accompanying drawings, which are incorporated in and constitute a part of this specification, illustrate embodiments of the invention and together with the description, serve to explain the principles of the invention.

BRIEF DESCRIPTION OF THE DRAWINGS

FIG. 4A shows a left-sided, posterior, full-thickness skull resection outlined by a cut region and the low-profile intercranial device (LID) of FIG. 2 being inserted into the resected portion of the skull. FIG. 4B shows the resulting implantation of the low-profile intercranial device (LID) following FIG. 4B.

DESCRIPTION OF THE EMBODIMENTS

Reference will now be made in detail to the present embodiments, examples of which are illustrated in the accompanying drawings. Wherever possible, the same reference numbers will be used throughout the drawings to refer to the same or like parts.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all sub-ranges subsumed therein. For example, a range of "less than 10" can include any and all sub-ranges between (and including) the minimum value of zero and the maximum value of 10, that is, any and all sub-ranges having a minimum value of equal to or greater than zero and a maximum value of equal to or less than 10, e.g., 1 to 5. In certain cases, the numerical values as stated for the parameter can take on negative values. In this case, the example value of range stated as "less that 10" can assume negative values, e.g. −1, −2, −3, −10, −20, −30, etc.

The following embodiments are described for illustrative purposes only with reference to the figures. Those of skill in the art will appreciate that the following description is exemplary in nature, and that various modifications to the parameters set forth herein could be made without departing from the scope of the present invention. It is intended that the specification and examples be considered as examples only. The various embodiments are not necessarily mutually exclusive, as some embodiments can be combined with one or more other embodiments to form new embodiments.

In CCI-based cranioplasty reconstruction, surgeons are rebuilding or reconstructing portions of the craniomaxillofacial skeleton to correct pre-existing deformities (e.g., following trauma decompression) and/or defects created by various etiologies such as tumor extirpation or trauma. The defects of the skull and/or facial bones, following bony resection are all concerning to a patient desiring complete reconstruction and visual harmony consistent with his/her pre-operative appearance. As such, this novel method and delivery system will be valuable to both instances of the missing cranium and/or facial bones. This could be valuable for those, for example, with trigeminal neurolagia requiring cheek bone resection and LID placement for local delivery of pain medicines to help control debilitating chronic disfiguring pain with all battery-powered components confined only to within the space of the missing bone.

Figure 1:
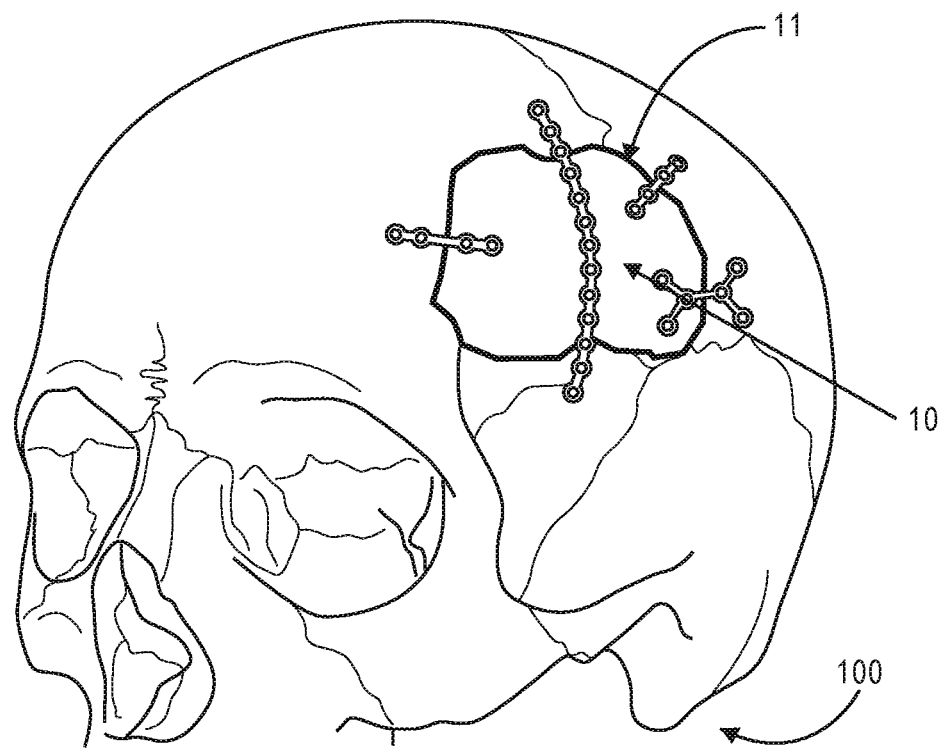
FIG. 1 illustrates a resulting "CCI-based cranioplasty reconstruction" with rigid fixation

Preoperative imaging such as CT or MRI may be used to identify the patient's cranial bone anatomy—which would make it quite feasible to design each LID in patient-specific fashion (as is done currently)—so as to address each patient's clinical care algorithm—both from a skull bone perspective and form an underlying regional brain pathology perspective. CCI-based surgery is currently planned using virtual pre-operative imaging to help identify an area of interest (e.g., a tumor) of the anatomy requiring reconstruction. For "single-stage cranioplasty" involved skull pathology requiring resection, bone cuts are planned/created virtually pre-operatively and a custom implant is designed, pre-fabricated, molded, and shipped to the surgeon to help fit into the resected region. The surgeon then attaches the CCI into the resected area using standard plates and screws. Computer-assisted guidance and custom implant position confirmation allows the surgeon to streamline this complicated process via intraoperative navigational guidance, for example, as described in International Patent Application No. PCT/US14/67656, filed on Nov. 26, 2014 entitled "Computer-Assisted Craniomaxillofacial Surgery". The result shown in FIG. 1 is an implant 110 that has an exact fit and is absent of gaps along the periphery 11 of the "implant-cranial bone interface" of the patient's skull 100.

The thickness of the CCIs (i.e., low-profile intercranial devices (LID) 300 in accordance with the present invention) can be preselected and in many instances CCIs have a thickness of around 4-12 millimeters (areas of strategic bulking 310b for concomitant temporal hollowing correction allow for extra implant thickness and in turn increased space for LID utilization wherein, and as described below in more detail, LID utilization requires the low-profile intercranial device 300 (as opposed to a "static" conventional CCI) comprises a base portion 310 and at least one cavity 323 configured to accept at least one functional component 322 associated with the base portion 310). Additionally, as related to their ideal proximity to the brain, CCIs may be imparted with functional capabilities as described for the novel methods and devices described herein. Accordingly, described herein are implants that are configured with functionality beyond structural support and sit comfortably within the boundaries of the anatomical skull defect. In some embodiments, such implants may be referred to as low-profile intercranial devices (LIDs).

As used herein, the term "functional component" or "functional cells" means any therapeutic hardware or compositions including, but not limited to, medicines to treat any patient-specific illness, or electronic, mechanical, imaging modality and/or electro-mechanical device to remotely monitor (e.g., via Wi-Fi connectivity) or intervene any specific neurologic illness, including imaging, monitoring, electrostimulation, radiation therapy, polarized light/laser neuronal modulation devices. The term "functional" denotes the fact that these CCIs are unlike current custom cranial implants, in that they have the capability to provide an additional purpose(s) or function other than as simply serving as a safe custom-shaped skull replacement via, for example, local drug delivery, or monitoring, such as brain monitoring or local electric stimulation—versus the current static CCI (SCCI), which is "static" in form and serves only to replace missing bone and provide cerebral protection from injury with ideal form and appearance post-reconstruction.

For example, LIDs may include one or more types of devices (i.e., functional component/cells) for delivery of local medicines, one or more types of valuable neurologic hardware like imaging modalities capable of providing real-time neuroimaging (e.g., ultrasound, optical coherence tomography, etc.), intracranial pressure (ICP) monitors with remote capabilities, small implanted radioactive seeds capable of long-term, chronic delivery of radiation to prevent local tumor recurrence, and/or functional wiring/battery/power source for deep brain stimulation and two-way feedback. In some embodiments, imaging modalities, such as optical coherence tomography (OCT), and/or high definition duplex ultrasound (U/S), may be stored and fossilized within the device. Any and all light/laser beams emitting from or transmitted to functional components in the device are unhindered. Such imaging modalities can provide remote imaging to both the patient and healthcare provider in areas of various brain pathologies like tumor growth, brain swelling, or stroke-like bleeding. In some embodiments, remote EEG and/or ICP pressure sensor hardware may be impregnated within the LID so that EEG tracings and/or intracranial pressure readings can be obtained remotely at any time, thereby alleviating any form of hospital admission or geographic constraints challenging optimal neurological treatment. In some embodiments, continuous EEG and intracranial pressures may be stored either locally for later access or accessed in real-time transmission, for example, via remote access through a communications link such as a wireless e.g., Wi-Fi connection by a remote server. As such, trends in patient health (e.g., EEG tracings, ICP readings, blood flow to damaged brain, etc.) may be monitored and more efficiently assessed by a healthcare team—therefore drastically reducing the financial burden of re-admitting these complex patients to hospitals. For example, in some embodiments, functional wires, pressure sensors, radioactive seeds, and/or low profile batteries may be incorporated in the LID as part of an on-board, "anatomically-shaped" skull-based computer, capable of controlling a built-in, remote-controlled, electronic monitoring system for novel assistance with electrophysiology measurements initiated via internet communication, such as through a secure Wi-Fi connection, between a remote computer and the functional component (e.g., on-board computer) of the LID. In another example, one of the functional components incorporated with the LID can comprise an on-board, embedded console connected to an electrode array with attached silicon needles and which may be disposed within the LID to help record electrical impulses of neurons inside the brain and/or provide stimulus to help bypass spinal cord paralysis and/or help to prevent Alzheimer's disease.

Additionally, functional components of the LIDs described herein may be configured with wireless/internet connectivity so as to be activated remotely to (by either healthcare provider, patient, or family/friend/caretaker), for example, release patient-specific electrical stimulation (e.g., electrical cortical brain stimulation), neuroimaging of underlying brain, biofeedback, radiation therapy, and/or medicines stored within the implant (placed at time of LID fabrication) and then delivered locally into or onto the brain in an unprecedented fashion to circumvent the BBB and/or to provide real-time, essential brain monitoring or radiation therapy of patients to drive future care—such as instances of brain tumor recurrence and increased CNS seizure activity, or any other visual brain pathology developments (i.e. Alzheimer's, Parkinson's, etc).

Figure 2:
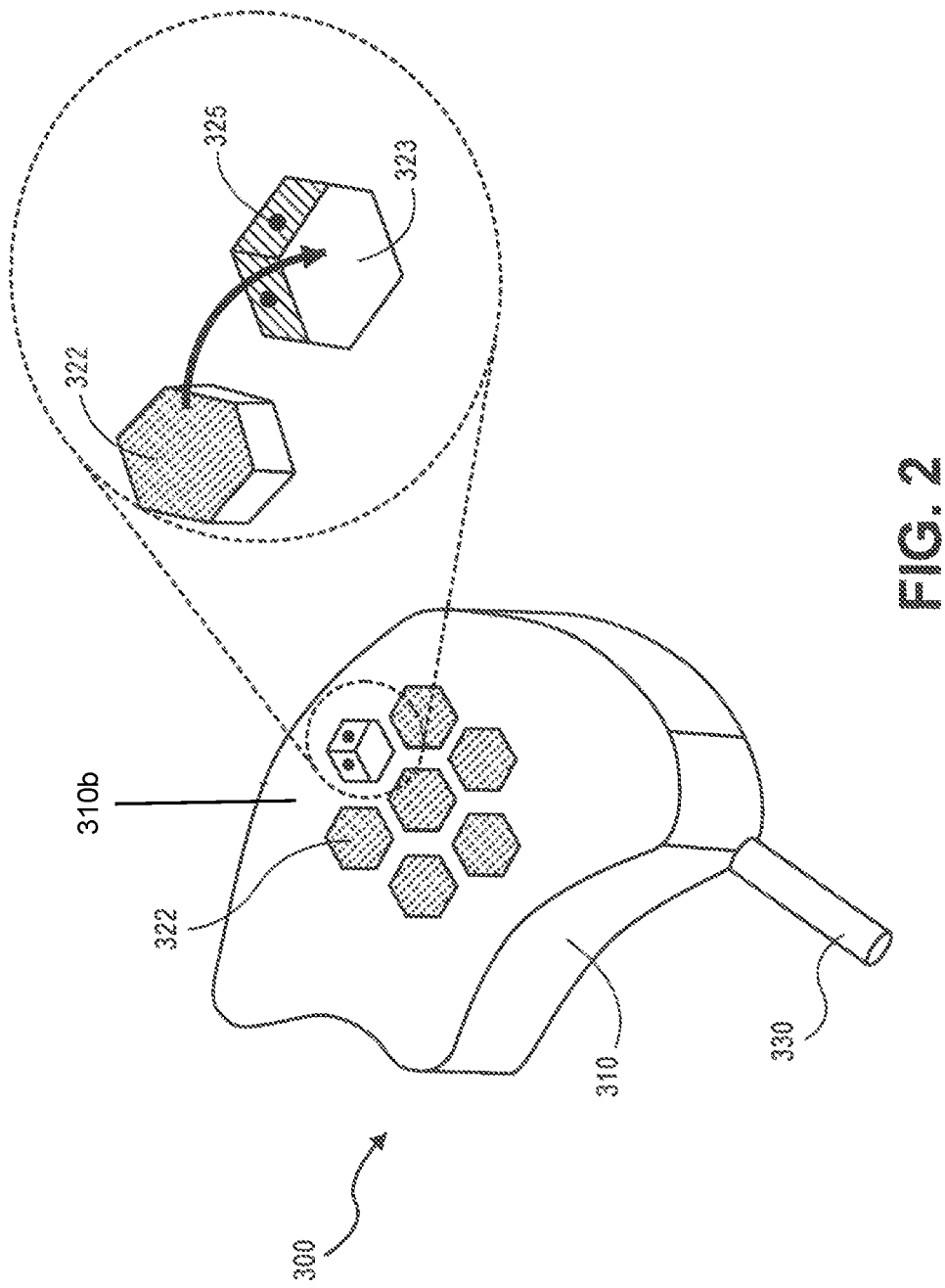
FIG. 2 is a low-profile intercranial device (LID) of an embodiment.

The concept of using LIDs (as opposed to "static" conventional CCIs), for all scenarios including "single-stage cranioplasty" (i.e. true defect size unknown), "second-stage cranioplasty" (i.e. true defect size is known in advance), or even for patients in need of local medicinal or radiation delivery for brain pathology—is exciting due to their many potential functions following placement and holds major potential for disease treatments currently hindered by scalp-related radiation problems and/or the BBB—including Parkinson's, Alzheimer's, brain tumors, and epilepsy. Accordingly, in an embodiment shown in FIG. 2 is a low-profile intercranial device (LID) 300 that comprises a base portion 310 (e.g., a housing) at least one cavity 323 associated with the base portion, and at least one conduit 330. The cavity 323 is configured to accept at least one functional component 322. In an embodiment, the conduit 330 has a first end in communication with the at least one cavity (not visible) and a second end. In an embodiment, the first end of the conduit 330 is in communication with the at least one functional component. In an embodiment, at least a portion of the at least functional component may be encased in the base portion.

In an embodiment, the functional component 322 comprises a medicinal therapeutic and the at least one conduit comprises a first end in communication with the at least one cavity and configured to accept the medicinal therapeutic and a second end configured to dispense the therapeutic to a patient. The conduit 330 can deliver medicinal therapeutic to the brain, for example, a diseased portion of brain parenchyma, a dead-space cavity following brain tumor resection, a blood vessel, neuron or ventricle. The at least one conduit can comprise polymer tubing. One example of a conduit is a catheter.

In an embodiment, the functional component comprises a physiological condition intervention system and the at least one conduit is configured to transmit a signal between the functional component and a patient. For example, the signal can be a chemical signal, an electronic signal, a magnetic signal or an optical signal. The functional component may be selected based on patient-specific pathology requiring treatment.

The functional component may, therefore, be disposed on a surface of or disposed within base portion 310. For example, the functional component may be disposed in a preformed one of cavity 323, which may be formed as fully or partially enclosed void-space portions of the implant, such as compartments), may be hermetically sealed within the implant, or may be incorporated in situ such as while forming the implant around it (e.g., during deposition of the implant material on or around the functional component 322). In an embodiment, the functional component is detachably connected to the base portion, for example, to replace the functional component with a functional component of the same type or a different one of a functional component, or to service the functional component.

The device 300 may be a custom, three-dimensional cranial or craniofacial implant made of either alloplastic materials or biologic, tissue-engineered cells of a being, such as a recipient being on whom the surgical procedure is performed. For example, base portion 310 may comprise a polymer, metal, bioengineered material, or combinations thereof, including but not limited to titanium mesh, porous hydroxyapatite (HA), polymethylmethacrylate (PMMA), polyether ether ketone (PEEK), tissue-bioengineered construct, man-made alloplastic material, a tissue engineered construct porous polyethylene (Medpor) and/or combinations thereof.

In an embodiment, the base portion may have a geometry that substantially conforms with, for example, a resected portion of the being's anatomy. For example, specifications of the base portion geometry may be provided for fabrication of a patient-specific base portion. In an example, fabrication of such a patient-specific base portion may be performed by a third party. In such an example, measurements of an anatomical area of interest are recorded during a planning stage, and the measurements of the base portion geometry are provided to a $3^{rd}$ party for fabrication. Subsequently, the $3^{rd}$-party-manufactured base portion may be attached to a patient. In such a method a clinician may be required to modify the base portion due to errors, tolerance variations, or changed circumstances such as changes in the geometry of the anatomical feature of interest since the time of initial measurements. Fabrication may be performed via any suitable known methods for forming modifying the base portion materials described above, for example, subtractive or additive manufacturing process. In another example, fabrication of a patient-specific base portion may be performed in-situ such as during surgical procedure. In such a method, a non-customized "blank" sample of base portion material, such as any of the materials described above, may be manipulated automatically or manually. Such a base may be formed using additive manufacturing techniques such as 3D printing or an off-the-shelf "blank" of base portion material may be manipulated manually.

Another example for making a base portion can include a computer-assisted, surgical method. Here, the base portion may be formed as an implant. The method can include attaching a reference unit that includes a first trackable element to a first anatomical feature of a being's anatomy, detecting a location of at least the first trackable element with a detector, and accessing a first computer-readable reconstruction of the being's anatomy. The detector may be configured to provide at least one signal corresponding to a detected location of at least the first trackable element. The first computer-readable may include a first updatable orientation, wherein the first updatable orientation may be updated in response to the at least one signal. The method may further comprise generating a second computer-readable reconstruction of an implant, the second computer-readable reconstruction comprising a second updatable orientation; assessing a size-mismatch between at least one dimension of a portion of the first computer-readable reconstruction corresponding to a selected anatomical feature of the being's anatomy and at least one dimension of the second computer-readable reconstruction; and tracing cut lines on the implant based on the size-mismatch such that an anatomical discrepancy at an area of removal or reconstruction of the anatomical feature is minimized at a preselected tolerance. Such a method may further comprise attaching a second trackable element to an implant; detecting a location of the second trackable element with the detector, wherein the at least one signal further corresponds to a detected location of the second trackable element; accessing a second computer-readable reconstruction of an implant, the second computer-readable reconstruction comprising a second updatable orientation, wherein the second updatable orientation is updated in response to the at least one signal; and superimposing the second computer-readable reconstruction on the first computer-readable reconstruction.

Another example for making a base portion can include resizing a "blank" during surgery. Here, the base portion may be formed as an implant. The method can include detecting a first location of a reference unit comprising a first trackable element with a detector, the detector configured to provide an at least one signal upon detecting the first trackable element of the reference unit, wherein the reference unit is associated with a location of a reference anatomical feature of a being's anatomy; accessing a computer-readable reconstruction of the being's anatomy, the computer-readable reconstruction of the being's anatomy comprising a first updatable orientation, wherein the first updatable orientation is updated in response to the at least one signal; accessing a computer-readable reconstruction of an implant comprising a second updatable orientation; detecting a location of a pointer tool comprising a second trackable element with the detector, the detector further configured to provide an at least one other signal upon detecting the second trackable element of the pointer tool, wherein the pointer tool is associated with a location of an anatomical feature of interest; accessing at least one computer-readable reconstruction of a trace, the trace corresponding to a geometry of the anatomical feature of interest based on updated detected locations of the pointer tool; and superimposing the at least one updatable, computer-readable trace on the computer-readable reconstruction of the implant. The method can further include displaying the computer-readable reconstruction of the trace, for example, by projecting the computer-readable reconstruction of the trace onto the implant. The method can further include marking the implant with a marking tool at points on the implant on which the computer-readable reconstruction of the trace is projected. The method can further include removing portions of the implant adjacent to an implant surface on which the computer-readable reconstruction of the trace is projected. Alternatively, an image based on at least one computer-readable reconstruction of the being's anatomy can be superimposed onto an implant, and a clinician may remove portions of the implant adjacent to the superimposed image so that a base portion having a geometry that substantially conforms to the being's anatomy is formed.

In another example a method for forming a base portion can include forming with an autonomous manufacturing device. The method includes accessing a first computer-readable reconstruction of a being's anatomy; accessing a second computer-readable reconstruction of an implant; accessing a third computer-readable reconstruction comprising the first computer-readable reconstruction superimposed with the second computer readable reconstruction; generating at least one computer-readable trace from a point cloud; and forming an implant with an autonomous manufacturing device, wherein the autonomous manufacturing device forms the implant into a shape defined by at least one dimension of the computer-readable trace. The method can further include generating a projected trace from the computer-readable trace, wherein the projected trace comprises a 2D or 3D projected trace and projecting the projected trace onto the implant.

Depending on the needs of a patient, at least one of functional component 322 may comprise low-profile, anatomically-shaped batteries, fossilized wiring system, encased imaging modalities, fossilized radioactive therapy seeds, and/or neurologic medicines stored locally within an inner portion of the device 300 (such as prefilled void spaces of the implant) while the structural integrity of the implant itself is not affected. In an embodiment, the functional component 322 may be a vital sign monitor, OCT image monitor, intracranial pressure (ICP) monitor, a remote imaging monitor or combinations thereof. Temperature control monitors may be included to monitor battery core temperatures and allow cut off measures in case of an alarm condition for the batteries being reached. In some embodiments, at least one of functional component 322 may be an electrical impulse generator, OCT image recorder, ICP reader, radioactive seed(s), or medicine dispensing device positioned in compartments formed within the confines of the implant. Each such functional component may be configured to deliver a therapeutic by way of a conduit, which may be, for example, a wire or catheter (i.e. IVC). In other embodiments, at least one of functional component 322 may be selected from various monitoring devices, for example, those with ICP or radiographic capabilities (e.g., local OCT or duplex ultrasound of underlying brain to assess for tumor recurrence), and may positioned in the device, such as in a cavity of the device which may be formed as a compartment configured to accept a functional component.

In an embodiment, at least one of functional component 322 may comprise biosensors (e.g., one-way or two-way biosensors) that provide real-time biofeedback and critical imaging of the brain when and if needed post-operatively via intracranial pressure (ICP) sensors. In addition, at least one of functional component 322 may be configured to provide immediate, life-saving pathophysiology-specific intervention when and if necessary, for example, with a remote control controlled by a physician/surgeon and/or patient's caretaker (family/friend). At the same time, the outside dimensions of the custom implant may remain the same exact size and shape as conventional implants used currently for time-tested, large-sized cranial or craniofacial reconstruction in pre-existing skeletal defects and connect via remote capabilities like Wi-Fi or Bluetooth—thus avoiding the modern day challenges of conventional implants that lead to premature removal related to scalp breakdown, infection and ultimate removal.

The conduit 330 may be in mechanical, electromagnetic, magnetic, radioactive, electronic or fluidic communication with at least a portion of the device 300 on one end and with a patient on the other end. For example, the at least one conduit 330 may have a first end in communication with the at least one cavity, the at least one of functional component 322, or both, and may have a second end in mechanical, electronic or fluidic communication with the patient, for example, the patient's neuron, blood vessel and/or ventricle. The conduit 330 may be a dispensing tube, wire, battery, fiber optic wire, radioactive seed, shunt, pump, vessel or an intraventricular or intravenous catheter (IVC) and may be inserted at the time of LID-based skull reconstruction. While not limited to any particular embodiment, the conduit 330 can provides for transit of a therapeutic, such as patient-specific and illness-specific medicine and/or computer-guided responsive stimulation from a functional component of the LID to a biological element of a being. For example, electrical impulses (signals), local radiation, and/or medicine may be transported from functional component 322, through the conduit 330, and directly into the brain cavity (following tumor resection), a neuron, blood vessel, or ventricle directly, thereby circumventing, among other things, the blood brain barrier. In other words, the device 300 with the conduit 330 provides immediate intra-neural or intra-thecal or intra-vascular delivery through catheters, biosensors and wiring intimately connected to the device, for example, in the functional component.

In an example, conduit 330 may be a coupling device that includes an input and an output for directing cerebrospinal fluid (CSF) or blood through preselected chambers of a functional component. Valves may be incorporated in the device 300 or along conduit 330, or within the functional component(s) 322 to designate flow direction of the CSF or blood. In an example, the valves may be CSF valves as these have sizes that are compatible with the LIDs of the embodiment. Exemplary ones of such valves include the Ultra VS, "Flow regulating valve mini" available from Integra NeuroSciences of Plainsboro, NJ and may be as small as 13 mm×3.8 mm×3 mm.

While not limited to any particular medicine or radioactive element or neurostimulation hardware or imaging modality, the functional component 322 may comprise anti-brain tumor, anti-seizure, anti-bleeding, anti-Alzheimer's anti-Parkinson, anti-hydrocephalus, and anti-ADHD medications—all of which is based on the patient's exact needs prior to implant design and manufacturing. While not limited to any particular monitoring, the functional component may be configured to provide vital sign and intracranial pressure (ICP) monitoring and may be able to provide life-saving, immediate, battlefield-like intervention when needed, for example, for members of the military or civilian police. In an example, at least one of the functional components of a LID could provide for intra-thecal delivery of morphine (i.e. pain relief at time of life-threatening injury) or norepinephrine (i.e. a sympathomimetic stimulant in time of fighting), administered upon an electromagnetic (e.g., Wi-Fi) signal activating a controller that initiates dispensing of such medicinal therapeutic from the functional component, for example, to those in the battlefield and/or civilian trauma environment (e.g., police, firemen) sustaining life-threatening injuries and/or in extreme pain on the verge of dying or in need of aided energy or strength at time of warfare.

Figure 3A:
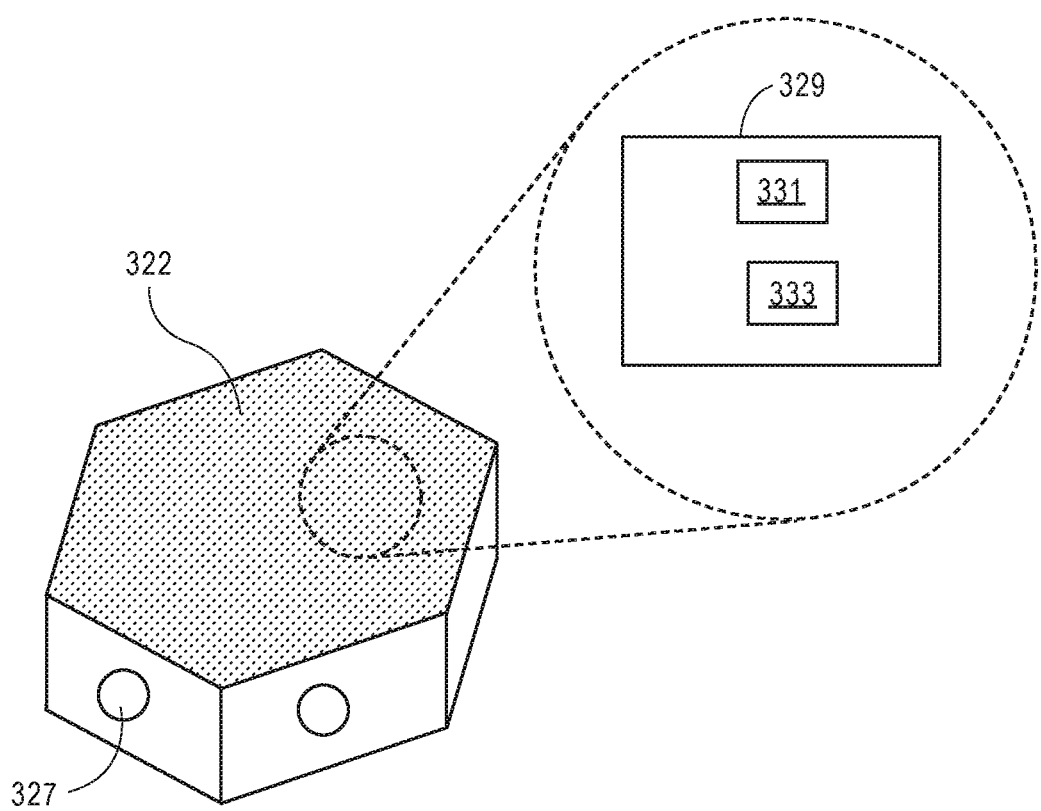
FIG. 3A is a close up view of functional component of the LID of FIG. 2 according to an embodiment.

As shown in FIG. 3A, the functional component 322 may include one or more ports 327. The one or more ports may provide, for example, electronic access to a central core, such as a controller including, for example, a processor and memory, and additionally, a wireless module so that the controller is configured for wireless connectivity, or additional connection portals. The one or more ports 327 may have a uniform size, shape, or both to so that other devices may connect with other ones of the functional components 322 of the LID device Depending on the need, the at least one port 327 may be configured for use as an interface for instruments delivering refills of medicines, devices for charging on-board batteries, devices for uploading software updates to on-board computers, or for engaging with and replacing the functional component. In an embodiment, the one or more ports 327 may be in communication with conduit 330 or with one or more ports of another one of the functional component. The at least one port 327 may be at least one access port for accessing, for example, a computer or electronics of the functional component, or medicinal composition stored in the functional component.

The device 300 may include structural internal support features. For example, the base portion may include internal supports through an internal portion of the base, such as pre-made PMMA endo skeletons, titanium endo skeletons, boxes, containers, scaffold, framework, traditional "green bread board" circuits, small pre-made PMMA pillars, titanium rods or rebar, screws, among other structural supporting features. Additionally, the device 300 functional components, which may include a battery-powered platform, can be strategically placed within the dead space area to optimize available volume and utilization, and at the same time, retain strength and protection to the underlying brain.

In an embodiment, the functional component 322 may include a gyroscope (digital or analog) to provide location precision, orientation, etc. In an embodiment, such location/orientation information can provide for triangulation for precision civilian care.

The functional component 322 may be configured with wireless (e.g., Wi-Fi/Bluetooth) and/or internet connectively, for example, Wi-Fi so that they may be controlled remotely or provide remote monitoring by collecting data and transmitting the data wirelessly back to the physician/surgeon/radiologist/hospital as described below. Furthermore, the implant could house a separate computer with various functions for prevention and/or immediate treatment/correction of certain neuropathology. Energy for LID function can be achieved through various methods such as perpetual motion used for wrist watches by way of kinetic energy, or could be simply based on low-profile, long-duration batteries (i.e. lithium) such as in the case of current cardiac pacemakers. In a future stage of this invention, there may be a role for anatomically-shaped batteries with patient-specific curvatures (i.e. battery shapes custom built for each patient) to better align with the contours of the skull anteriorly or posteriorly to optimize the implant's low-profile shape.

The communication between the LID and its patient could be valuable in instances where symptoms develop—for example Alzheimer's disease or Parkinson's tremor or epilepsy with signs of pre-syndrome for impending dementia, tremor, or seizure. As such, as shown in FIG. 3A, the device 300 of the embodiments may include a functional component 322 that has an on-board functionality 329, such as such as a medicinal therapeutic 331, a physiological condition intervention system 333, or both.

In an example, the medicinal therapeutic comprises optogenetic proteins, radiation therapy, chemical therapy, or a combination thereof. Exemplary medicinal therapeutics comprise one or more therapies selected from the group consisting of anti-tumor, anti-seizure, anti-parkinson, anti-hydrocephalus, anti-ADHD, anti-alzheimer's, anti-pain, energy-enhancing, and combinations thereof.

In an embodiment, the physiological condition intervention system 333 is configured for computerized monitoring of a physiological condition such as abhorrent seizure activity, intercranial pressure elevation, or both for example by monitoring of a diseased portion of brain parenchyma, a dead-space cavity following brain tumor resection, a blood vessel, a neuron, a ventricle or combinations thereof. Accordingly, the physiological condition intervention system 333 may be configured to provide acute neurological intervention comprising medicinal therapy, electro-stimulation therapy, radiation therapy or a combination thereof, such as to provide neuron modulation via optic sensors. In an example, conduit 330 is in at least one of fluidic, electrical, magnetic, or optical communication between the physiological condition intervention system and a patient. As one example, the computerized monitoring comprises imaging, such as optical coherence tomography (OCT), intracranial pressure (ICP) monitoring, vital sign monitoring or combinations thereof. Therefore, the physiological condition intervention system may include at least one of a vital sign monitor, OCT image monitor, ICP monitor, remote imaging monitor or combinations thereof. Exemplary physiological condition intervention systems may include an electrical system, remote imaging system, encased battery-powered system, radiation system, responsive neurostimulation system, neuromodulation system (e.g., battery-powered neuromodulation), drug delivery system, or combinations thereof. Such systems may include a medicine delivery device, an electrical signal delivery device, an image capture device, a radioactive seed device, an energy storage device, a computing device, or combinations thereof. In an example, the physiological condition intervention system comprises at least one of an electrical energy source, an electrical energy detector, electromagnetic energy source, an electromagnetic energy detector, a therapeutic composition source, or combinations thereof. In an embodiment, the electrical energy source generates an electrical signal. In an embodiment, the electromagnetic energy source generates an optical signal, such as laser or other electromagnetic energy, for example, visible light. In an embodiment, the electromagnetic energy detector captures images. In an embodiment, the therapeutic composition source delivers medicinal therapeutic. The at least one electrical signal, optical signal, image capture, or medicine may include one or more therapies selected from the group consisting of anti-tumor, anti-seizure, anti-parkinson, anti-hydrocephalus, anti-ADHD, anti-alzheimer's, anti-pain, energy-enhancing, and combinations thereof.

Therefore, the physiological condition intervention system can include a power source and a sensor powered by the power source, wherein the sensor is configured to sense a physiological condition. In an example, the physiological condition intervention system comprises at least a portion of an imaging device, for example, an OCT system or optogenetic receivers.

As described above, the device 300 may further include a controller (not shown), for example, a computer comprising a processor and a memory. The controller may be included in the functional component or may be disposed in another location of device 300. The at least one controller may be configured to initiate or terminate dispensing of the medicinal therapeutic 331 stored in the functional component Other on-board hardware can include a wireless connectivity module so that the controller may be configured for wireless connectivity so as to be remotely monitored, activated or both. It is notable that each of the functional component may be in communication with at least one other of a functional component via ports 327 (e.g. at least one electrode, fluid ports, optic fibers, combinations thereof) and/or may be accessed, for example, by way of a smart phone or hospital computerized system, for purpose of charting timeline of neurological disease and response as examples via communications links 325 disposed within the implant and which may couple with the ports 327 of the functional component. Similarly, a physician or caretaker could tap into the LID remotely to help obtain local information related to the underlying brain—such as tumor recurrence, remote EEG (electroencephalogram) recordings, or seizure activity. Either way, the wireless (e.g., Wi-Fi) capabilities allow endless therapeutic options currently not available to patients or surgeons.

The at least one functional component 322 may include a plurality of functional components. Each of the plurality of functional components 322 may be the same or different. For example, the functional component can include a first functional component and a second functional component, wherein the first functional component is the same or different than the second functional component. For example, one or more of the functional component may be a battery stimulation device, radioactive treatment device, a remote imaging device or a drug delivery device and one or more of other ones of a functional component may be a monitoring device or responsive electrostimulation device.

Figure 3C:
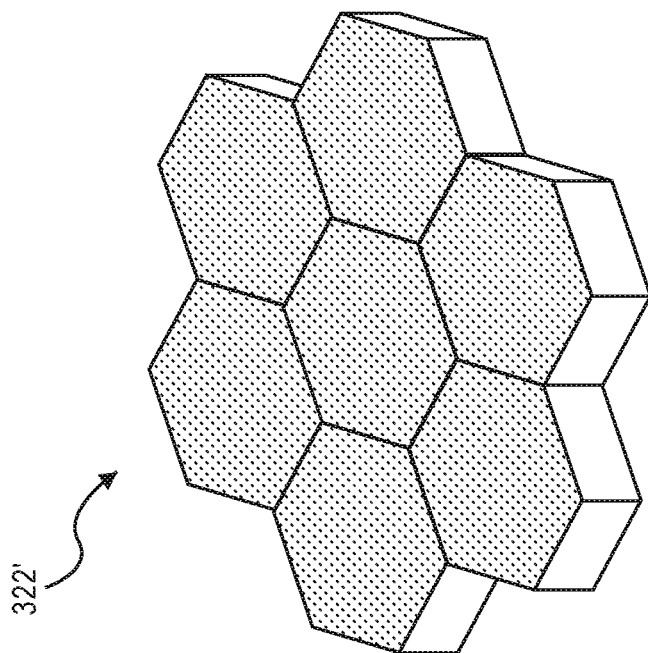
FIG. 3C illustrates a configuration for a multiplicity of functional components that may be interconnected to form a 7-cell cluster and/or encased battery unit.
Figure 3B:
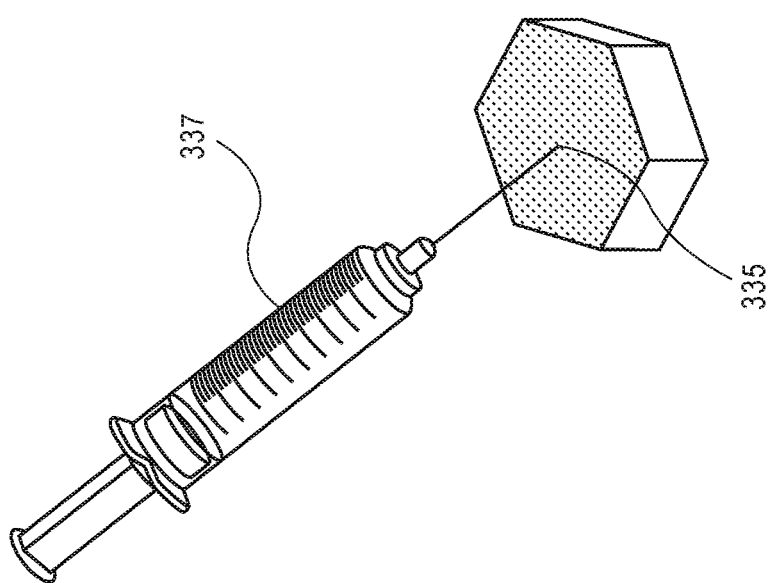
FIG. 3B illustrates a syringe delivering medication to a functional component of an embodiment having a porous body or port for accepting the syringe needle.

As illustrated in FIG. 3B-3C, the functional component 322 may be a plurality of functional components that share a uniform shape and may be physically, electrically or communicatively (e.g., via a computer network) coupled to one another, such as clustered together as an interconnected multi-cell functional component 322'. In an example, the plurality of functional components are electrically coupled to one another. The implant, including the functional component thereof, may be made of a permeable material capable of accepting minimally-invasive battery changes (e.g., a local slot for battery exchange below scalp with small incision) or subcutaneous delivery of medicines via injection into a port within the LID, for example, using a syringe 337 to deliver through a surface 335 of the functional component 322 as shown in FIG. 3B. In an embodiment, therefore, the functional component 322 comprises at least one porous surface through which material, such as medicine, may be delivered, for example, via a syringe needle penetrating into a storage volume of the functional component or a local slot for minimally-invasive component exchange.

The functional component 322 of the embodiments may be provided in various shapes. In an embodiment, each one of the functional components 322 is the same shape. In another embodiment, one functional component may be the same or different shape as another component. In one embodiment, one or more of the functional component may be a uniform shape. By using a uniform shape for the functional component 322, for example, a polyhex, for the functional component 322 of device 300 of the embodiments, collaboration with multiple vendors is more predictable. By creating, defining, and standardization this new approach to treatment, multi-functions are expected for each implant and they may be provided in a multi-piece configuration. A hexagon, triangle, or square for example all allow interlacing shapes to efficiently occupy a larger space. The functional component 322 may be configured so as to not have deleterious effects on the strength and integrity of the implant. Rather, the functional component 322 may be configured to maximize the potential space within an implant while at the same time, maximizing the structural integrity of the implant. These embodiments described then may be defined as one of, or a combination of, interlocking hexagonal shapes working together or independently. For example, a hexagon with 1 cubic centimeter volume may be the standard unit of measure to build on. As shown in FIG. 3C, a device 300 may include a 7-cell cluster of functional components 322 (i.e., a multi-cell functional component 322'). In such a cluster, one or more of the functional components may store medicine (Rx), batteries, or sensing devices. However, it is noted that the embodiments are not limited to clusters of 7-functional components and may be adjusted accordingly to accommodate larger devices as needed.

In addition to the features described above, device 300 may include a button or manual switch on the implant surface to open a battery or component replacement slot which allows for minimally invasive component updates/replacements (e.g., battery change) to the implant rather than full removal/replacement. For example, a button or manual switch may be located on a side of the implant that is accessible via a small minimally-invasive scalp incision. The button or pop-open slot can provide access to the core of the LID, or could include a self-sealing port for which a special needle, such as a Huber needle, could be used for two-way access (delivery of neurologic medicine into brain tissue or brain blood vessels or even blood draw or CSF removal from out of the brain).

Figure 4A:
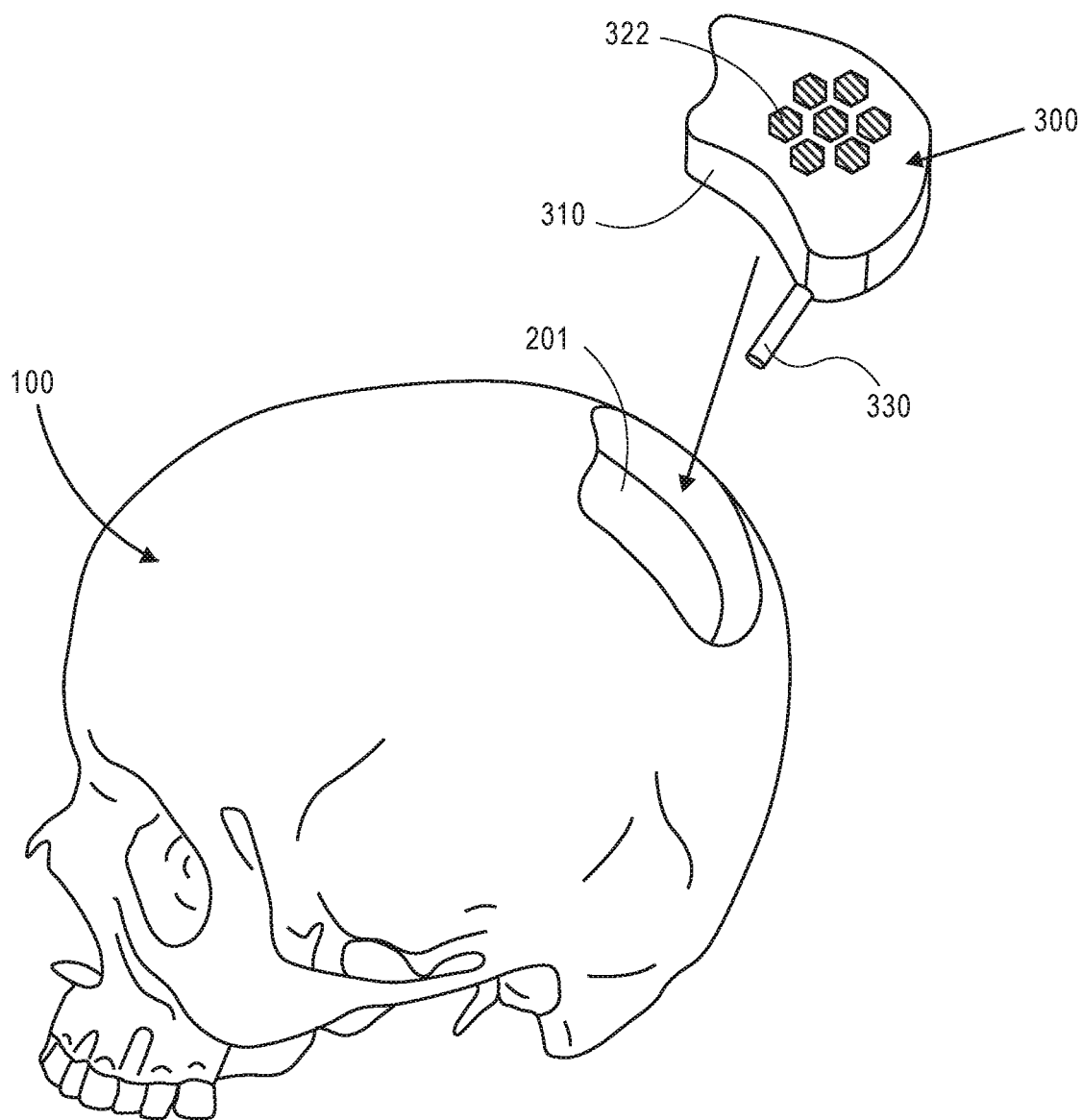
FIGS. 4A-4B illustrate a method of attaching a LID, such as the implant of FIG. 2.

A method of an embodiment may include attaching the LID to a preselected anatomical feature of interest, such as to a patients anatomy surrounding pathological or oncological defect sites directly over previously-resected epilepsy or brain tumor areas, such as in the case of benign (i.e. meningioma) or malignant (i.e. glioblastoma) brain neoplasms, and/or within large cranial defects lying directly over previous regions of stroke, trauma, aneurysmal bleeding, and/or bone flap osteomyelitic infection. For example, the LID may be attached to a portion of a being's craniomaxillofacial skeleton with rigid fixation plates/screws and/or biocompatible glue. As such, each of these previous illnesses may benefit from local electrode stimulation or drug delivery specific to the original pathology—such as blood thinners for someone who had a thrombotic stroke or stem cell delivery for someone with recent trauma. At least some embodiments described herein can be used for the immediate surgical repair of cranial defects and/or to remove normal skull just so that the local electrical or medicine delivery option can be available if needed. For example, embodiments described herein may be used for designing, forming, modifying and/or implanting functional customized craniofacial implants (i.e., LIDs) following benign/malignant brain or skull neoplasm (tumor) resection (i.e., herein referred to as "single-stage implant cranioplasty"). As shown in FIG. 4A, a skull opening during such procedures will expose the underlying dura and brain. Thus, an implant so attached to the skull can be disposed in direct, overlying proximity to the brain as shown in FIG. 4B.

As shown in FIG. 4A, the device 300 may be inserted or replaced at a resected portion 201 of a skull during a surgical procedure, such as a surgical implantation procedure for various forms of craniomaxillofacial surgery and/or neurosurgery including an implant-based cranioplasty. The functional, custom skull implant of the embodiments may be configured for real-time delivery of responsive electricity, OCT imaging, ICP monitoring, EEG tracing, radiation therapy, and/or pathology-specific medicines that have not previously been deliverable or effective through the blood-brain barrier in order to treat either paraplegic (unilateral extremity weakness) or Alzheimer's disease (for enhanced memory function), Parkinsonian patients (e.g., delivery of medicines for tremor control), brain tumor patients (delivery of anti-tumor medicines and/or local radiation), epilepsy patients (anti-seizure medicines for both control and emergency rescue), hydrocephalus patients (e.g., to reduce intracranial pressures for both control and emergency situations), and/or deep cranial infection patients (antibiotic and antifungal medicines).

Figure 4B:
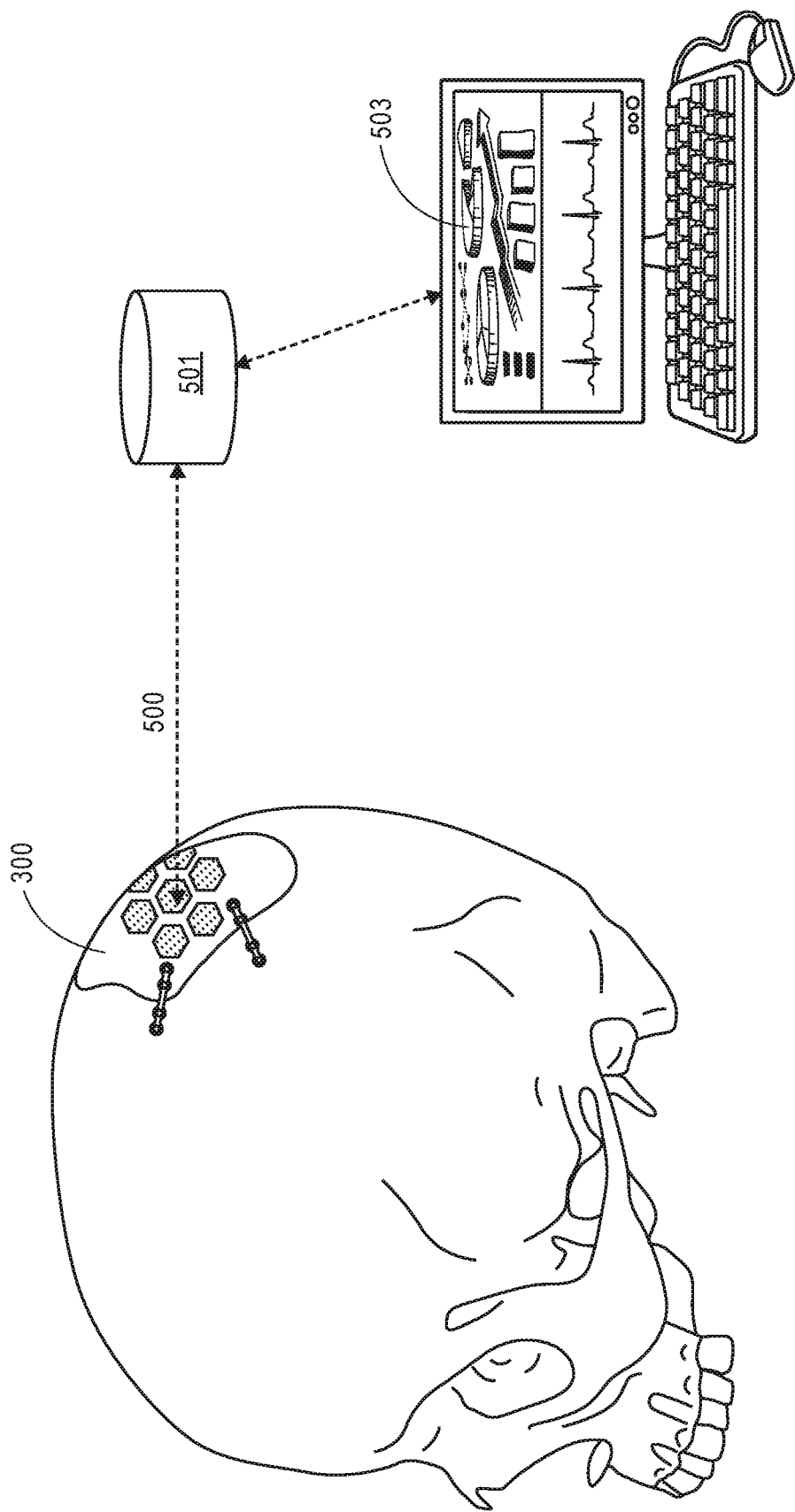

As shown in FIG. 4B, the device 300 can be provided with communications capability so as to communicate (as indicated by double-headed dashed-line 500) with a computer 503, via for example, a server 501. While not limited to any particular embodiment, such communication may be via electrical communication (such as via a USB cable) or via electromagnetic communication via Wi-Fi, Bluetooth, or the like. In one example, computer 503 may include a processor that executes software instructions for communicating with the functional component 322 of device 300. As such, remote monitoring of brain activity and/or tumor recurrence could drastically reduce healthcare costs associated with hospital-based imaging such as MRI and could remove the need to have IVs placed for contrast administration—since the necessary dye could be delivered by the LID and imaging could also be done remotely by the LID simultaneously. While not limited to any particular embodiment, computer 503 may be a desktop computer, notebook computer, smart phone, tablet, a virtual reality device, a mixed reality device and server 501 may be a cloud server. Computer 503 may communicate with the device 300, for example, functional components 322 of the implant, via the internet. The functional component 322 may be activated remotely, for example, via signals generated in computer 503. One example is analogous to a 24-hour cardiac heart monitor for which records heart activities for a certain time period. With the LID of the embodiments, the implant device could be designed to monitor electrical activity, supranormal intracranial pressures, acute stroke-like bleeding, brain tumor recurrence, or aberrant seizure activity for a certain timeframe, and then at any time, the intervening physician, could download a recorded database of all activities related to specific intervention (i.e. subclinical seizure activity). Computer 503 may display data associated with signals generated by the functional component 322 as it monitors a patients on whom the device 300 is attached.

As described herein, provided is a low-profile intercranial device (LID). A LID of the embodiments can solve a multitude of existing complications resulting in a major reduction in neurological patient visits and re-admissions (e.g., as related to brain pathology exacerbations) to doctor's offices/hospitals as the implant is configured to perform brain imaging scans, deliver local head irradiation for brain tumor recurrence prevention, deliver medicines in real-time to the central nervous system, and/or provide biometric feedback testing in terms of vital signs—thereby saving the US healthcare system billions of dollars each year related to periodic testing, imaging, neurological interventions, and/or unnecessary hospitalizations. Accordingly, embodiments described herein may provide the potential to eradicate the need for labor-intensive electroencephalograms (EEGs) and spinal taps by providing a self-sealing valve in subcutaneous tissue plane (comparable to a "portacath" used commonly for cancer patients requiring frequent intravenous drug administrations) within the LID which will be attached directly under the scalp with easy access. One advantage of the LIDs of the embodiments is that they are fabricated for each patient-specific scenario—so that each functionality is selected preemptively and individually customized for all patients depending on their pathology-specific scenario. Furthermore, the LIDs of the embodiment can also simultaneously correct cranial or craniofacial deformities by filling skeletal defects created by neurosurgery or craniofacial plastic surgery. Therefore, the LIDs described herein could be placed within a pre-existing skull or facial skeletal defect or could be placed in areas of normal bone, independent of knowing that a neurosurgical patient will need the additive benefits of the LID of the embodiments.

In an example, the dispensing tube of the embodiments may be an intra-ventricular or intravenous catheter (IVC). For example, in an embodiment there is an LID that comprises an IVC. A lumen portion of the IVC has direct communication to the medicine(s)—so that a patient in which the LID is implanted could have pre-scheduled dosing of quantity and time intervals controlled by either an inside computer (a computer portion of the implant preprogrammed with dosage information) or outside signaling (e.g., Wi-Fi, communication via smartphone).

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

In at least one embodiment, an LID is configured to provide for wireless ICP monitoring. In an example, wireless ICP monitoring provides patients with a comfortable option for remote sensing of abnormal elevated intra-cranial pressures, as similar to either cases of acute intensive care unit (ICU) stays (typically less than 30 days) within peri-operative period, or in instances of long-term pressure monitoring for chronic conditions such as obstructive hydrocephalus, for instance. Such an LID having wireless ICP monitoring capabilities prevents the need for hospital admission and direct connection to a machine device for sensor testing.

In at least one embodiment, an LID is configured to provide endocranial imaging by way of, for example, OCT, for imaging underlying brain tumors or brain tumor resection cavities following surgery. Such functionality provides a way to, for example, remotely monitor new growths within the brain following resection of disease. In one example of a system for providing endocranial imaging, the functional component may comprise a CPU, ICP, or battery, and a component configured to monitor vitals and/or cerebral blood flow to the region.

In at least one embodiment, an LID is configured to provide embedded "lead" stimulation. For example, at least one functional component may comprise features similar to the RNS® System (available from Neuropace of Mountain View, CA), for example, a cranially implantable programmable RNS® Neurostimulator that senses and records brain electrical activity. As such, an LID of the embodiments may be configured to detect previously identified electrical patterns in the brain and to deliver electrical stimulation to the brain to interrupt such patterns before the patient experiences clinical seizures. In an example, such an LID may comprise a functional component that includes a responsive Neurostimulator and one or two leads that connect to the Neurostimulator.

In at least one embodiment, an LID may include local radiation therapy options for brain tumor patients for high risk of local recurrence. This advancement, by incorporating radioactive seeds within the LID, functions to eradicate all risks for scalp-related complications such as dermatitis and/or exposed cranial hardware related to the standard external beam radioactive therapy modalities often used today. In such an embodiment, an LID is a radioactive therapy device placed below the scalp for treatment of brain tumor pathology using a radio-lucent encasement floor (i.e. bottom part of LID such as a bottom base portion) and a radio-opaque ceiling (i.e. top part of LID such as an upper base portion).

The terms "coupled," "connected," and "connecting" refer to "in direct connection with" or "in connection with via one or more intermediate elements or members." Furthermore, to the extent that the terms "including", "includes", "having", "has", "with", or variants thereof are used in either the detailed description and the claims, such terms are intended to be inclusive in a manner similar to the term "comprising." As used herein, the phrase "at least one of" or "one or more of", for example, A, B, and C means any of the following: either A, B, or C alone; or combinations of two, such as A and B, B and C, and A and C; or combinations of three A, B and C.

What is claimed is:

1. A functional, low-profile intercranial device (LID), comprising:
 a base portion comprising a cranial or craniofacial implant having a geometry that is configured to conform with a resected portion of a skull of a patient and has a thickness configured to provide strategic bulking for concomitant temporal hollowing correction, the base portion including a curvature specific to that of the skull to ensure a fit with absence of gaps along a periphery of the base portion, and the base portion being configured to address a patient clinical care algorithm both from a skull bone perspective and from an underlying regional brain perspective such that the cranial or craniofacial implant is configured to correct deformities and/or defects by placement at least partially within the resected portion of the skull during a surgical procedure to replace missing bone and provide cerebral protection from injury;

at least one functional component;

at least one cavity formed within the base portion as a void space within the base portion, the at least one cavity configured to encase the at least one functional component; and at least one conduit comprising an end configured to be in communication with the at least one cavity, wherein an orientation of at least one of the at least one conduit or the at least one functional component is configured to be customizable for the patient.

2. The functional, low-profile intercranial device of claim 1, wherein the conduit is configured to provide for transit of a therapeutic from a functional component, of the at least one functional component, to a brain of the patient.

3. The functional, low-profile intercranial device claim 1, wherein the conduit is configured to provide for transit of computer-guided responsive stimulation from a functional component, of the at least one functional component, to a brain of the patient.

4. The functional, low-profile intercranial device of claim 1, wherein the at least one functional component is detachably connected to the base portion.

5. The functional, low-profile intercranial device of claim 1, wherein the conduit is configured to provide for transit of signals from a functional component, of the at least one functional component, to a brain of the patient.

6. The functional, low-profile intercranial device of claim 1, wherein the cranial or craniofacial implant is radiolucent.

7. The functional, low-profile intercranial device of claim 1, wherein the cranial or craniofacial implant comprises polymethylmethacrylate (PMMA), polyether ether ketone (PEEK), or polyethylene.

8. The functional, low-profile intercranial device of claim 1, wherein the cranial or craniofacial implant is a custom cranial or craniofacial implant.

9. A functional intercranial implant, comprising:

a base portion comprising a cranial or craniofacial implant having (i) a first portion with a geometry that is configured to conform with a resected portion of a skull of a patient to ensure a fit with absence of gaps along a periphery of the base portion and (ii) a second portion of increased thickness configured to provide strategic bulking for concomitant temporal hollowing correction, the second portion having space for accommodating a functional component, the cranial or craniofacial implant being configured to address a patient clinical care algorithm both from a skull bone perspective and from an underlying regional brain perspective such that the cranial or craniofacial implant is configured to correct deformities and/or defects by placement at least partially within the resected portion of the skull during a surgical procedure to replace missing bone and provide cerebral protection from injury; and a conduit comprising an end configured to be in communication with the functional component, an orientation of at least the conduit or the functional component being configurable to be customizable for the patient.

10. The functional intercranial implant of claim 9, wherein the functional component is configured to deliver a medicinal therapeutic.

11. The functional intercranial implant of claim 10, wherein the end is a first end configured to be in communication with the functional component to accept the medicinal therapeutic, and wherein the conduit further comprising a second end configured to dispense the medicinal therapeutic.

12. The functional intercranial implant of claim 9, wherein the conduit is configured to provide for transit of a therapeutic.

13. The functional intercranial implant of claim 9, wherein the conduit is configured to provide for transit of computer-guided responsive stimulation from the functional component.

14. The functional intercranial implant of claim 9, wherein the conduit is configured to provide for transit of signals from the functional component to a brain of the patient.

15. The functional intercranial implant of claim 9, wherein the cranial or craniofacial implant is radiolucent.

16. The functional intercranial implant of claim 9, wherein the cranial or craniofacial implant comprises polymethylmethacrylate (PMMA).

17. The functional intercranial implant of claim 9, wherein the cranial or craniofacial implant is a custom cranial or craniofacial implant.

18. The functional intercranial implant of claim 9, wherein the first portion has a thickness of around 4-12 millimeters.

19. The functional intercranial implant of claim 9, wherein the functional component is a medicinal pump.

20. The functional intercranial implant of claim 9, wherein the base portion comprises at least one porous surface through which a syringe needle can penetrate or at least one access port for accepting the syringe needle.

* * * * *

UNITED STATES PATENT AND TRADEMARK OFFICE
CERTIFICATE OF CORRECTION

| | | |
|---|---|---|
| PATENT NO. | : 12,150,858 B2 | Page 1 of 1 |
| APPLICATION NO. | : 17/357115 | |
| DATED | : November 26, 2024 | |
| INVENTOR(S) | : Chad Gordon | |

It is certified that error appears in the above-identified patent and that said Letters Patent is hereby corrected as shown below:

In the Claims

Claim 1:
Column 18, Line 64 change "1. A functional, low-profile intercranial device (LID)," to -- 1. A functional, low-profile intercranial device, --

Claim 3:
Column 19, Line 28 change "3. The functional, low-profile intercranial device claim 1," to -- 3. The functional, low-profile intercranial device of claim 1, --

Signed and Sealed this
Twenty-second Day of April, 2025

Coke Morgan Stewart
*Acting Director of the United States Patent and Trademark Office*